United States Patent [19]

Kesling

[11] Patent Number: 4,498,867
[45] Date of Patent: Feb. 12, 1985

[54] CONVERTIBLE ORTHODONTIC APPLIANCE

[75] Inventor: Peter C. Kesling, LaPorte, Ind.
[73] Assignee: TP Laboratories, Inc., Westville, Ind.
[21] Appl. No.: 575,657
[22] Filed: Jan. 31, 1984
[51] Int. Cl.³ .............................................. A61C 7/00
[52] U.S. Cl. ...................................... 433/16; 433/17
[58] Field of Search ............................. 433/16, 17, 13

[56] References Cited
U.S. PATENT DOCUMENTS
3,494,034 2/1970 Kesling .................................. 433/17
4,371,337 1/1983 Pletcher ................................ 433/10

Primary Examiner—Robert Peshock
Attorney, Agent, or Firm—Lee, Smith & Zickert

[57] ABSTRACT

An orthodontic appliance that is convertible to function in both light wire and edgewise techniques and which includes a sheath mountable on a tooth that may selectively receive any one of several wire receiving inserts. Each of the inserts is lockable to the sheath and thereafter removable so that the sheath, while still mounted on a tooth, can alternately be fitted with any one of several inserts. One of the inserts is formed to function as a light wire buccal tube, while another is formed to function as an edgewise buccal tube. A further insert is formed to function as an edgewise bracket.

2 Claims, 14 Drawing Figures

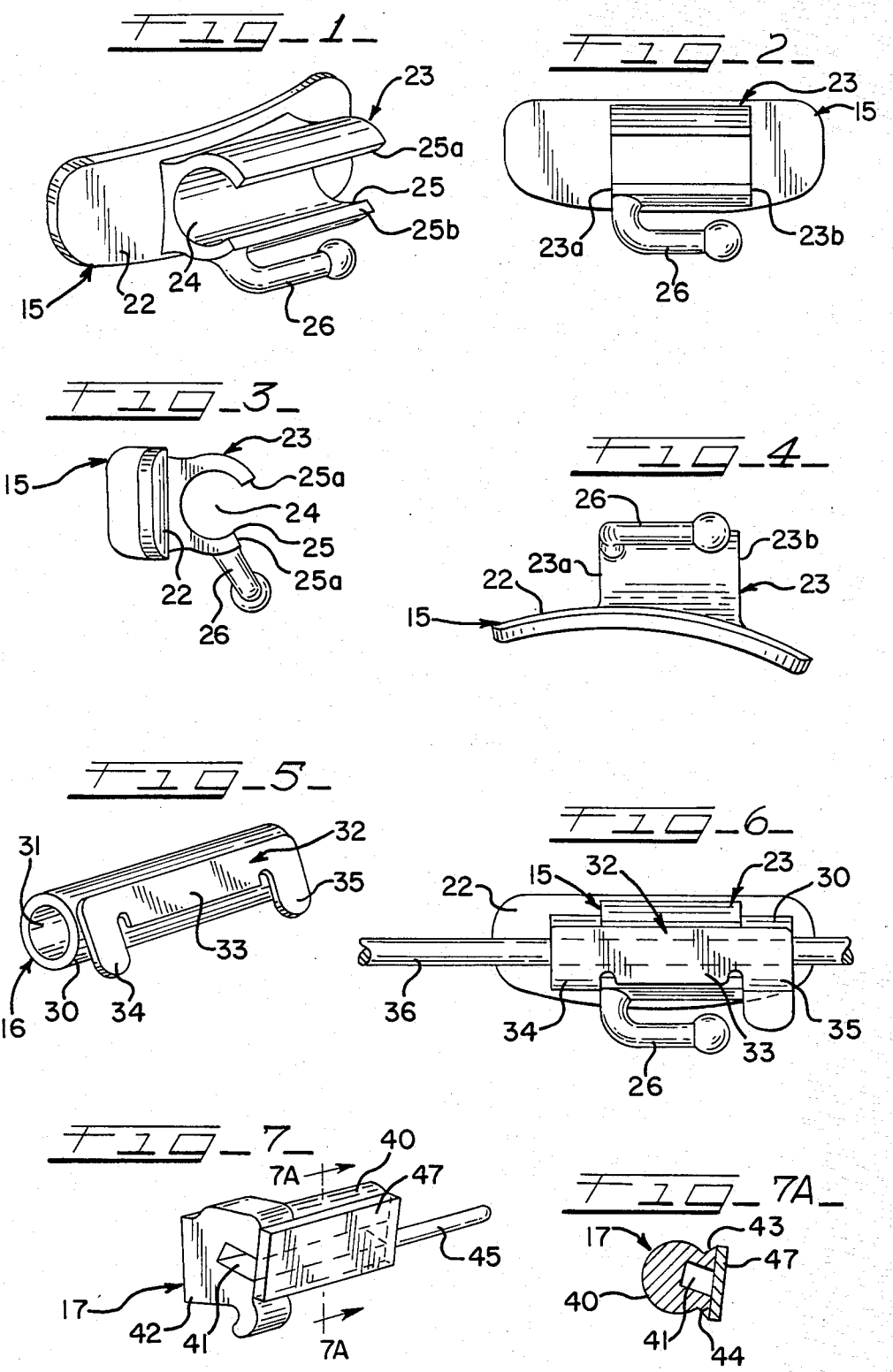

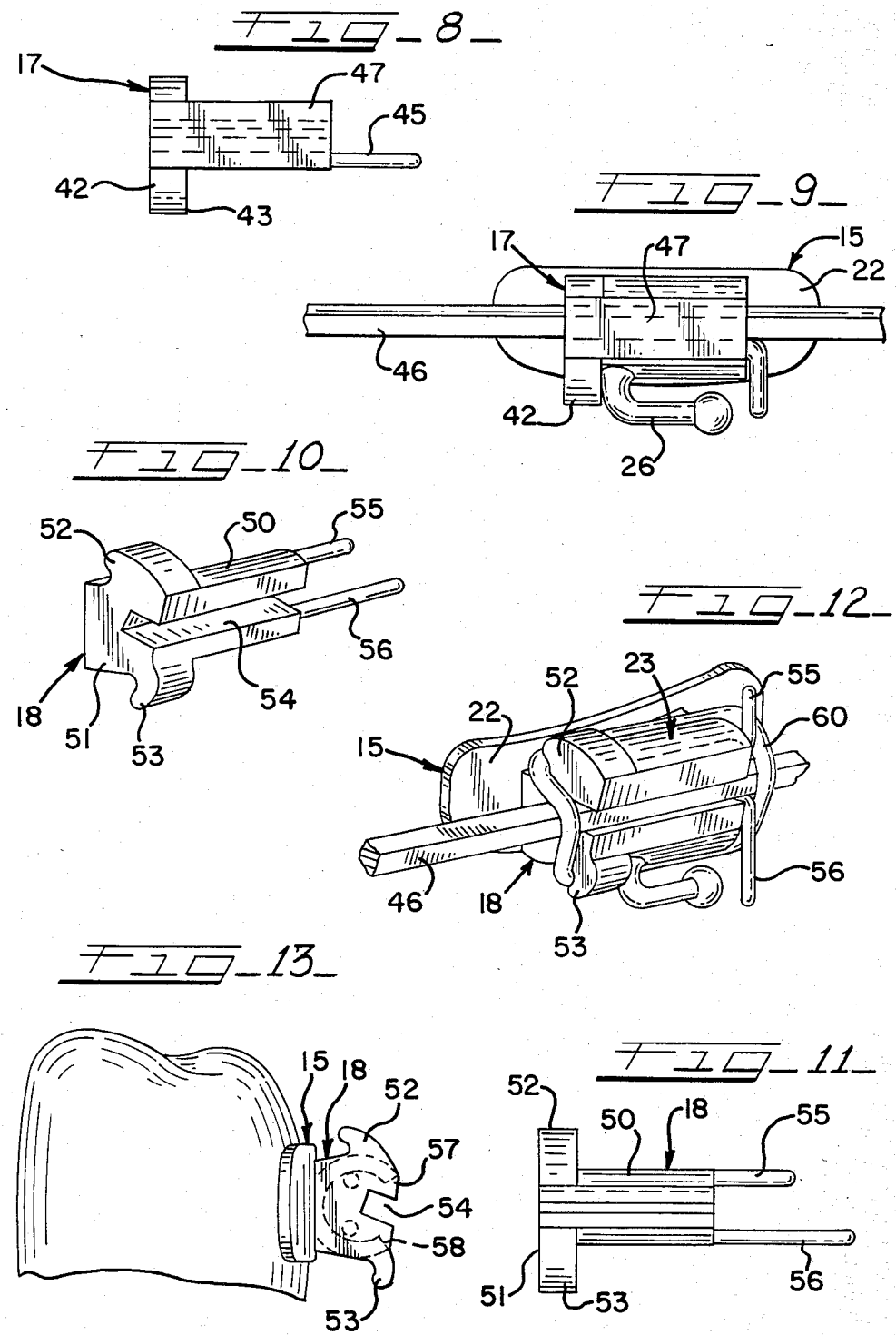

CONVERTIBLE ORTHODONTIC APPLIANCE

DESCRIPTION

This invention relates in general to an orthodontic appliance for use in light wire or edgewise systems, and more particularly to a convertible orthodontic appliance that may function as a light wire buccal tube, a rectangular or square wire buccal tube or a rectangular or square wire bracket.

Heretofore, there have been a number of orthodontic appliances that are convertible to function for either the light wire or edgewise systems, such as shown in U.S. Pat. No. 2,908,974. However, the appliance shown in this invention is bulky and in all forms always includes tie wings for locking the inserts in place and for also securing archwire to the inserts. Such bulky tie wings as shown in this patent contribute to the possible occlusal interferences which can cause damage to the appliance and/or discomfort to the patient. If the appliance is placed too low to avoid occlusal intereferences, it will irritate the gingiva and make the placement or removal of archwires extremely difficult.

The present invention overcomes the difficulties heretofore known in convertible appliances for use with both light wire and edgewise systems by incorporating the tie wings into the edgewise bracket insert, thereby providing tie wings only when needed and permitting a greater range of placement of the appliance on the tooth to minimize discomfort to the patient.

It is therefore an object of the present invention to provide a new and improved convertible orthodontic appliance for use in both edgewise and light wire systems which includes a sheath attachable to a tooth and a plurality of inserts to coact with the sheath and define appliances for use in achieving different functions.

It is a further object of the present invention to provide an orthodontic appliance for use in both edgewise and light wire systems including a sheath attachable to a tooth and a light wire buccal tube insert mountable on the sheath to coact therewith and define a buccal tube for the light wire system, an edgewise buccal tube insert to coact with the sheath and define a buccal tube for use in the edgewise system, and an edgewise bracket insert to coact with the sheath and define an appliance for receiving a rectangular or square wire.

Other objects, features and advantages of the invention will be apparent from the following detailed disclosure, taken in conjunction with the accompanying sheets of drawings, wherein like reference numerals refer to like parts, in which:

FIG. 1 is a perspective view of the sheath of the orthodontic appliance of the invention;

FIG. 2 is a buccal elevational view of the sheath shown in FIG. 1;

FIG. 3 is an mesial elevational view of the sheath shown in FIG. 1;

FIG. 4 is a bottom plan view of the sheath;

FIG. 5 is a perspective view of the light wire tube insert for the sheath;

FIG. 6 is a buccal elevational view of the sheath with the light wire buccal tube insert of FIG. 5 mounted in place and illustrating one of the bendable locking tabs in bent and locking position in solid and in unlocking position in phantom;

FIG. 7 is a perspective view of an edgewise system buccal tube insert for the sheath;

FIG. 7A is a cross-sectional view of the insert of FIG. 7 taken substantially along lines 7A–7A of FIG. 7;

FIG. 8 is a buccal elevational view of the buccal tube insert of FIG. 7;

FIG. 9 is a buccal elevational view of the edgewise buccal tube insert mounted in the sheath;

FIG. 10 is a perspective view of the edgewise bracket insert of the invention;

FIG. 11 is a buccal elevational view of the insert of FIG. 10;

FIG. 12 is a perspective view of the insert of FIG. 10 mounted in place on a sheath of the invention and illustrating an archwire ligated to the appliance; and FIG. 13 is an mesial elevational view of the assembly shown in FIG. 12.

Referring now to the drawings, the convertible orthodontic appliance of the invention includes a sheath 15, a light wire buccal tube insert 16, an edgewise buccal tube insert 17, and an edgewise bracket insert 18. Preferably the sheath and inserts will be made of suitable stainless steel. As will be more further explained below, each of the inserts coacts with the sheath to define an appliance capable for use in a particular wire receiving function whereby the appliance may be converted to provide different wire receiving functions by removing one insert and replacing it with another insert, all while the sheath remains in mounted position on the tooth. Accordingly, the appliance can be used throughout the treatment of a patient where it would be possible to begin treatment with the light wire system and end treatment with the edgewise system, or vice-versa.

The sheath 15 includes an elongated base 22 contoured to matingly fit the buccal surface of a molar tooth. This base could be welded or soldered to a tooth band or to a mesh base. If attached to a tooth band, it will be appreciated that the band will be suitably cemented to a tooth. If attached to a mesh base, it can be appreciated that the base may be directly bonded to a tooth in the usual manner by a suitable bonding material.

A cylindrically shaped body 23 is suitably attached to the base 22 and extends outwardly from the base and includes a mesiodistally extending opening 24 for slidably receiving an insert. The mesiodistally extending body 23 also includes a mesiodistally extending slot 25 on the side away from the base. Both the opening and the slot are of uniform dimension along their entire lengths. The slot 25 defines parallel extending edge faces 25a. A ball-ended hook 26 is mounted on the body 23 for purposes of anchoring a suitable elastic member or the like and normally the hook will face distally. The hook is an optional accessory for the sheath, and it may be appreciated that it is generally disposed at the gingival side of the body and toward the buccal, although it may be disposed at the occlusal side or the body may be provided with hooks at both sides.

For purposes of further describing the invention, the forward end of the body 23 and designated 23a may be considered the mesial end, while the rearward end 23b may be considered the distal end for purposes of orientation in the mouth.

Mounting of the sheath on a tooth will normally be accomplished whereby the mesiodistally extending opening 24 will extend substantially perpendicular to the long axis of the tooth.

The light wire buccal tube insert 16, shown particularly in FIGS. 5 and 6, includes a tube-shaped body 30 having a mesiodistally extending round opening 31 extending therethrough for receiving the distal end of an archwire.

An orientation and locking member 32 is suitably secured to the tubular body 30 such as by welding or soldering and includes an anti-rotation bar 33 extending parallel to the axis of the tubular body and coacting with the opposed edge faces 25a of the sheath body 23 to prevent relative rotation between the sheath and insert. Opposed bendable locking tabs 34 and 35 are provided at opposite ends of the bar 33 and spaced apart a distance substantially equal to the mesiodistal length of the sheath body 23. When the insert is in place on a sheath, as shown in FIG. 6, the tabs may be bent back against the tubular body and act as stop members at the mesial and distal ends of the sheath body 23 to prevent mesiodistal movement of the insert relative to the sheath and thereby selectively lock the insert to the sheath. It will be appreciated that the outer dimension of the tubular body 30 is such that it will easily slide within the cylindrical opening 24 of the sheath in mating relation therewith. While the anti-rotation bar 33 prevents relative rotation between the insert and the sheath, it also functions to maintain the bendable tabs 34 and 35 at the buccal side of the appliance to assure access to the tabs for bending them between locking and unlocking positions. It may be further appreciated that one of the bendable tabs may be bent into locking position before insertion into the sheath, and when it abuts the respective end of the sheath body, a suitable tool may be used to bend the other tab into locking position, thereby selectively locking the insert to the sheath. If one desired to remove the insert, it will be a simple matter to bend outwardly one of the tabs and then slide the insert from the sheath. FIG. 6 also illustrates a round wire 36 in position on the appliance, and it will be appreciated that the diametrical dimension of the opening through the light wire buccal tube insert will normally be substantially greater than that of the wire.

The edgewise buccal tube insert 17 shown in FIGS. 7, 8 and 9 includes a body having a cylindrically formed portion 40 sized to slidably mate with the mesiodistally extending opening 24 in the sheath body 23, a mesiodistally extending rectangular or square wire receiving opening 41, an enlarged head portion 42, and a bendable locking tab or spur 45. The head portion 42 is preferably positioned on the mesial end of the insert and serves as a stop when the insert is placed in the sheath by engagement with the mesial end 23a of the sheath body. As seen particularly in FIG. 9, the bendable tab 45 is bent down over the distal end 23b of the sheath body to selectively lock the insert 17 to the sheath. Thus, the head portion 42 and the bendable tab 45 serve to prevent mesiodistal movement of the insert with respect to the sheath, and a rectangular archwire 46 is illustrated in FIG. 9 in place as it would be received in the wire receiving opening of the insert. The opening would be sized so that the archwire would be matingly received and rotation between the archwire and the appliance would not be permissible. The angular disposition of the archwire receiving opening 41 may be as illustrated or otherwise as desired depending upon the case being treated. Further, this insert would normally be made by milling a piece of material to form the opening 41 which would then be closed by the attachment of a cover plate 47 to define a buccal tube. Lips 44 and 45, which are best seen in FIG. 7A, coact with the edges 25a and 25b of the sheath body 23 and prevent relative rotation between the insert 17 and the sheath and orient the insert with respect to the sheath. The insert could also be made in one piece.

The edgewise bracket insert 18 includes a cylindrically formed body portion 50 that would matingly fit in the mesiodistally extending opening 24 of the sheath body 23. An enlarged head portion 51 having formed thereon upper and lower tie wings 52 and 53 is disposed at one end of the body portion 50. A mesiodistally extending archwire receiving slot 54 of rectangular cross section is formed longitudinally of the insert, and a pair of bendable locking tabs 55 and 56 extend from the distal end of the cylindrical body portion 50. Preferably, the enlarged head portion 51 is disposed at the mesial end of the body as illustrated and will serve as a stop member against the mesial end of the sheath body when the insert is disposed in the sheath, as shown in FIG. 12. Upper and lower lips 57 and 58 are provided along the buccal side of the cylindrical body portion 50 to engage the edges 25a and 25b of the sheath body 23 and prevent relative rotation between the insert and the sheath, as illustrated particularly in FIG. 12, thereby precisely orienting the insert relative to the sheath. The depth and angular position of the archwire slot 54 may be as illustrated or in any other suitable fashion to produce forces on the wire as desired. It may be further appreciated that the slot 54 is always positioned in alignment with the sheath slot 25 so that the rectangular archwire may be inserted into the slot after the insert has been mounted in the sheath.

As seen particularly in FIGS. 10 and 11, the bendable tabs 55 and 56 are not of the same length although it may be appreciated they could be of the same length. The occlusal tab 55 is preferably of a shorter length so that it does not extend into the occlusion area and become damaged during mastication. When the tabs 55 and 56 are bend over the distal end of the sheath body at right angles to the insert, as illustrated in FIG. 12, they first function to selectively lock the insert in place on the sheath. Secondly, they serve as tie wings, and as illustrated in FIG. 13, a ligature 60 is mounted on the appliance over the tie wings 52 and 53 and the bendable tabs 55 and 56 to retain the archwire 46 in position on the appliance.

From the foregoing, it can be appreciated that the appliance of the invention is convertible to one for use as a light wire buccal tube, an edgewise buccal tube, or an edgewise bracket to accommodate the various wire receiving functions attributed to these inserts and for permitting the versatility of usage without necessitating the need for remounting an entirely different appliance on the tooth. One insert may be readily removed and replaced with another to change from one wire receiving function to another.

It will be understood that modifications and variations may be effected without departing from the scope of the novel concepts of the present invention, but it is understood that this application is to be limited only by the scope of the appended claims.

I claim:

1. An orthodontic appliance for use in the light wire or edgewise system comprising, a sheath attachable to a tooth along an axis generally perpendicular to the long axis of the tooth and including an elongated mesiodistally extending body having a mesiodistally extending cylindrical opening and a mesiodistally extending slot on the side away from the tooth, and a wire receiving insert removably mountable in the opening of said sheath, and said insert including, a generally cylindrical body matingly slidable into said sheath opening, means coacting with said sheath for selectively locking the insert to the sheath, ligating wings on one end, said selective locking means on the other end and including a pair of bendable locking tabs which when bent over the corresponding end of said sheath function as ligating wings, means coacting with the sheath slot to prevent relative rotation between the insert and sheath, and a mesiodistally extending wire receiving opening or slot, said wire receiving opening being shaped to receive a rectangular or square wire and be open horizontally through the sheath slot to permit the appliance to function as an edgewise bracket, and said means preventing rotation being disposed to align the insert opening with the sheath slot.

2. A convertible orthodontic appliance for use in the light wire or edgewise system comprising, a sheath attachable to a tooth along an axis generally perpendicular to the long axis of the tooth, said sheath including an elongated mesiodistally extending body having a mesiodistally extending cylindrical opening and a mesiodistally extending slot on the side away from the tooth, a light wire buccal tube insert removably mountable in the opening of said sheath to coact therewith and define a buccal tube for the light wire system, and edgewise buccal tube insert removably mountable in the opening of said sheath to coact therewith and define a buccal tube for the edgewise system, an edgewise bracket insert removably mountable in the opening of said sheath to coact therewith and define an edgewise bracket for the edgewise system, said edgewise bracket insert further including a rectangular or square wire receiving slot aligned with said sheath slot and ligating wings, and each of said inserts having means coacting with the sheath slot to prevent rotation of the insert in the sheath and means for selectively locking the insert to the sheath.

* * * * *